(12) United States Patent
Bianco (10) Patent No.: US 11,583,655 B2
(45) Date of Patent: Feb. 21, 2023

(54) SYSTEM AND METHOD FOR PROSTATE TREATMENT UNDER LOCAL ANESTHESIA

(71) Applicant: SmartBlate, LLC, Miami Lakes, FL (US)

(72) Inventor: Fernando J. Bianco, Miami Lakes, FL (US)

(73) Assignee: SmartBlate, LLC, Miami Lakes, FL (US)

( * ) Notice: Subject to any disclaimer, the term of this patent is extended or adjusted under 35 U.S.C. 154(b) by 601 days.

(21) Appl. No.: 16/497,226

(22) PCT Filed: Mar. 26, 2018

(86) PCT No.: PCT/US2018/024404
§ 371 (c)(1),
(2) Date: Sep. 24, 2019

(87) PCT Pub. No.: WO2018/183217
PCT Pub. Date: Oct. 4, 2018

(65) Prior Publication Data
US 2020/0108222 A1 Apr. 9, 2020

Related U.S. Application Data (60) Provisional application No. 62/476,751, filed on Mar. 25, 2017.

(51) Int. Cl.
*A61M 19/00* (2006.01)
*A61B 5/055* (2006.01)
(Continued)

(52) U.S. Cl.
CPC ............. *A61M 19/00* (2013.01); *A61B 5/055* (2013.01); *A61B 8/12* (2013.01); *A61B 8/5261* (2013.01);
(Continued)

(58) Field of Classification Search
CPC ......... A61M 19/00; A61B 2018/00547; A61B 8/12; A61B 8/5261; A61B 2018/00577
See application file for complete search history.

(56) References Cited

U.S. PATENT DOCUMENTS

| 9,597,145 B2 * | 3/2017 | Nelson | A61B 18/16 |
| 2008/0154253 A1 * | 6/2008 | Damasco | A61B 18/02 |
| | | | 606/20 |

(Continued)

OTHER PUBLICATIONS

Cerqueira ["Transrectal Ultrasound-Guided Prostate Biopsy: Conclusion About the Best Anesthetic Technique" Brazilian Archives of Naval Medicine, Rio de Janeiro, 69 (1): 60-63, Dec. 2008, pp. 60-63] (Year: 2008).*

(Continued)

*Primary Examiner* — Oommen Jacob
(74) *Attorney, Agent, or Firm* — Fleit Intellectual Property Law; Paul D. Bianco; Gary S Winer (57) ABSTRACT

A system and method for prostate cancer treatment under local anesthesia includes creating a superficial skin and subcutaneous block in a perineal area of a patient by administering a first anesthetizing agent; creating a deep nerve block under ultrasound guidance by administering a second anesthetizing agent, the second anesthetizing agent infiltrating cavernosal nerve bundle tissue and periprostatic space; and ablating prostate tissue. The office-based method, statistical models and computer generated treatment plans identify and ablate prostate tissue containing cancer through or via the perineum while preserving prostate function, and critical anatomical structures. Multiple technologies are integrated and processed to deliver a safe treatment procedure, under local anesthesia by integrating the information of magnetic resonance imaging and planning the ablative treatment using algorithms that ensure maximal precision in both killing cancerous tissue and preserving healthy tissue along with its corresponding function.

15 Claims, 10 Drawing Sheets

(51) Int. Cl.
*A61B 8/12* (2006.01)
*A61B 8/08* (2006.01)
*A61B 18/02* (2006.01)
*A61B 18/04* (2006.01)
*A61B 18/14* (2006.01)
*A61B 18/22* (2006.01)
*A61K 31/167* (2006.01)
*A61N 5/06* (2006.01)
*A61N 7/02* (2006.01)
*A61B 18/00* (2006.01)
*A61N 7/00* (2006.01)

(52) U.S. Cl.
CPC .............. *A61B 18/02* (2013.01); *A61B 18/04* (2013.01); *A61B 18/14* (2013.01); *A61B 18/22* (2013.01); *A61K 31/167* (2013.01); *A61N 5/062* (2013.01); *A61N 7/022* (2013.01); *A61B 2018/00547* (2013.01); *A61B 2018/00577* (2013.01); *A61B 2018/00613* (2013.01); *A61B 2018/00982* (2013.01); *A61B 2018/0212* (2013.01); *A61B 2018/048* (2013.01); *A61M 2210/166* (2013.01); *A61N 2007/003* (2013.01)

(56) References Cited

U.S. PATENT DOCUMENTS

| | | | | |
|---|---|---|---|---|
| 2010/0049031 A1* | 2/2010 | Fruland | ................. | A61B 18/16 |
| | | | | 600/439 |
| 2010/0049188 A1* | 2/2010 | Nelson | ............... | A61N 1/36071 |
| | | | | 606/34 |
| 2011/0106072 A1* | 5/2011 | Sundquist | .......... | A61N 1/36071 |
| | | | | 606/41 |
| 2014/0073907 A1* | 3/2014 | Kumar | ................... | A61B 34/10 |
| | | | | 600/407 |
| 2015/0038843 A1 | 2/2015 | Nishina | | |
| 2015/0209105 A1* | 7/2015 | Margallo Balbas et al. | ................ | |
| | | | | A61B 5/6886 |
| | | | | 600/301 |
| 2016/0000506 A1* | 1/2016 | Trachtenberg | ......... | A61B 18/22 |
| | | | | 606/10 |
| 2020/0108222 A1* | 4/2020 | Bianco | .................. | A61B 5/055 |

OTHER PUBLICATIONS

IPRP International Preliminary Report and Written Opinion for PCT/US2018/024404, dated Oct. 10, 2019.
International Search Report and Written Opinion for PCT/US2018/024404, filed Mar. 26, 2018.
Glass et al, Local Anesthesia for the Prostate Gland, Clinical Use of Local Anesthetics, www.intechopen.com, pp. 59-74, 2012.
Li et al, Local anesthesia for transrectal ultrasound-guided biopsy of the prostate: A meta-analysis, Scientific Reports, www.nature.com/scientificreports, 8 pages, 2016.
Written Opinion for PCT/US2018/024404 filed Mar. 26, 2018.
Local Anesthesia for the Prostate Gland (pp. 59-73); Allison Glass, Sanoj Punnen and Katsuto Shinohara; Department of Urology, University of California, San Francisco USA.
Local anesthesia for transrectal ultrasound-guided biopsy of the prostate; A meta-analysis; Scientific Reports; Mingchao Li, Zhengyun Wang, Hao Li, Jun Yang, Ke Rao, Tao Wang, Shaogang Wang & Jihong Liu.

* cited by examiner

SYSTEM AND METHOD FOR PROSTATE TREATMENT UNDER LOCAL ANESTHESIA

FIELD OF THE DISCLOSURE

The disclosure relates to a system and method for treatment of prostate cancer under local anesthesia.

BACKGROUND OF THE DISCLOSURE

A conundrum of questions has surrounded prostate cancer management where just in the United States over 200,000 men have received such diagnosis yearly in the last two decades alone. An unquantifiable research effort has been conducted by thousands of health care providers, investigators, and epidemiologists seeking to elucidate the trails from molecular origins of prostate cancer to its clinical virulent variants that pose a real mortality risk. In this process millions of patients across the globe have been treated by several means and all kinds of results have been reported.

Currently, prostate cancer screening practices are questioned, due to a significant harm versus benefit risk calculus. Standard biopsy procedures (transrectal) carry significant risk for infections, sample the prostate inadequately, lack precision of sampled area and do not allow appropriate access for direct treatment. Surgical approaches such as Open, Laparoscopic and Robotic Radical Prostatectomy have been shrouded with variability in outcomes. Even if the cancer treatment does result in successful removal of the cancerous tissue, current treatment approaches too often lead to detrimental quality of life (such as incontinence, loss of erection, and loss of ejaculation).

The current management conundrum leads patients to choose to either take no action and pursue surveillance measures or have physician treat the prostate gland completely. The latter leads commonly to significant losses of daily function such as the control of urination or the initiation of erections.

Accordingly, there exists a need for an integrated system and method for treatment of the prostate which minimizes adverse effects of the treatment.

SUMMARY OF THE DISCLOSURE

One aspect to the disclosure relates to a method for prostate cancer treatment under local anesthesia. The method comprises: creating a superficial skin and subcutaneous block in a perineal area of a patient by administering a first anesthetizing agent; creating a deep nerve block under ultrasound guidance by administering a second anesthetizing agent, the second anesthetizing agent infiltrating cavernosal nerve bundle tissue and periprostatic space; and ablating prostate tissue.

Another aspect of the disclosure relates to a system for prostate cancer treatment tinder local anesthesia. The system comprises: means for creating a superficial skin and subcutaneous block in a perineal area of a patient by administering a first anesthetizing agent; means for creating a deep nerve block under ultrasound guidance by administering a second anesthetizing agent, the second anesthetizing agent infiltrating cavernosal nerve bundle tissue and periprostatic space; and means for ablating prostate tissue.

Exemplary embodiments applicable to both the disclosed method and system are now described.

The first and second anesthetizing agent can be the same agent or different agents. In one embodiment, both include lidocaine solutions. The patient can be placed in a lithotomy position.

The superficial skin and subcutaneous block can be created by administering the first anesthetizing agent in a first perineal space, the first perineal space delimited by a perineal raphe medially, superiorly by an edge of a scrotum, laterally by a first gluteal crease and inferiorly by an anal verge; and administering the first anesthetizing agent in a second perineal space, the second perineal space delimited by the perineal raphe medially, superiorly by the edge of the scrotum, laterally by a second gluteal crease opposite the first gluteal crease, and inferiorly by the anal verge.

In order to monitor the treatment, real-time monitoring of the ablation with ultrasound imaging can be used. The ultrasound imaging can be obtained with a transrectal ultrasound probe, with the ultrasound probe attached to a stepper to control position and movement of the ultrasound probe. A grid can be attached to the stepper, the grid provided with indicia for identifying holes in the grid.

In addition to the ultrasound imaging, multi-parametric MRI imaging of the prostate and surrounding anatomy can be obtained. Fusion imaging can be produced by co-registration of the MRI imaging and ultrasound imaging.

In an embodiment, the fusion imaging includes an image of the grid. Further, the fusion imaging can include contours of the prostate and contours of prostate cancer lesions, in an exemplary embodiment, the fusion imaging shows a treatment plan with a planned location of a treatment probe for ablating prostate tissue.

Using the treatment plan, the treatment probe is inserted to the planned location.

Depending on the application, the treatment probe uses: high frequency ultrasound for tissue destruction; an electrical field, in which electricity flows allowing for irreversible electroporation and destruction of tissue; laser energy for tissue ablation; water vapor "steam" for tissue destruction; photodynamic energy that when activated destroy tissue that contains a pharmaceutical agent; nanoparticles, which destroy tissue; or cryoablation for tissue destruction.

In order to ensure placement, the actual position of the treatment probe can be compared to the planned location. Ablation of tissue can be monitored by comparing the treatment plan shown on the fusion imaging to tissue destruction shown on the fusion imaging.

In an embodiment, the treatment plan is created based on a model calculating and showing expected temperatures around tissue ablation zones. The model can be based on lesion location and lesion volume and treatment location and treatment volume. The model can additionally be based on distances from edges of a treatment zone defined by the treatment location and treatment volume to anatomical structures.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings (which form an integral part of the description and are to be read in conjunction therewith), in which the drawings show the justification and rationale behind the disclosed system and method; the three different components of the disclosed system and method (diagnosis, biopsy, and treatment); and some results of the disclosed system and method.

In the drawings.

DETAILED DESCRIPTION

As required, embodiments are disclosed herein; however, it is to be understood that the disclosed embodiments are merely examples and that the devices and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

In an embodiment, the disclosure relates to an office-based method of reaching prostate cancer tissue through or via the perineum, destroying prostate cancer tumors identified on a magnetic resonance imaging study and using transrectal ultrasound to monitor the process of destruction; in a safe manner, under local anesthesia.

The combined effect of the disclosed system and method is to reach and ablate prostate tissue containing cancer through or via the perineum while preserving prostate function, and critical anatomical structures such as the neurovascular bundles responsible for erections, the urethral sphincter and bladder neck that provides for preservation of continence and ejaculatory function, respectively.

Although there are a number of variations of the disclosed system and method, they share common characteristics as follows:

I. The use of fusion imaging-integration of two imaging studies (such as MRI and ultrasound) to destroy identified prostate cancer tumor tissue and monitor the procedure in real-time. The treatment plan, modeling and implementation is performed using the MRI information. The ultrasound information obtained is used to define, reach and monitor the treatment that is modeled by the processed MRI information.

II. The safety of the procedure: Performed with a novel local anesthesia block devised by the inventor. The safety of the procedure is also ensured by real-time monitoring using the fused MRI information and ultrasound information, governing the treatment delivery and may initiate and stop (automatically without human intervention; semi-automatically with human intervention after the human is alerted by the system; and/or manually by human intervention) the ablation process based on the individual characteristics of the patient prostate cancer.

III. Approach is applicable for several forms of energy including, but not limited to: cryoablation, microwave, irreversible electroporation, steam, and laser among others.

As a result of these common characteristics, benefits compared to known systems and methods) of the disclosed system and method include, but are not limited to:

1—Preservation of Urinary Continence

2—Subjective and Objective Improvement in Urinary Function

3—Preservation of Erectile Function

4—Preservation of Ejaculatory Function

5—Elimination/Ablation of cancerous tissue

6—Elimination of the need of general or spinal anesthesia and their adverse effect profiles 7—Expedited recovery 8—Decreased work loss 9—Improvement in psychological profile triggered by cancer diagnosis 10—Decreased risk to overtreatment 11—No loss to access and implementations of standard treatment (surgery, radiation, hormonal deprivation therapy) should they be required in the future.

The disclosed system and method provide a new approach for urologists and other practitioners that treat prostate cancer, to whom, to date, do not have knowledge that such approach is possible, feasible, reproducible, and effective. There is no steep learning curve and the system and method can be monetary rewarding.

The disclosure contemplates different variations of the various components, such as:

A. Any suitable ultrasound machines, such as those that employ hi-planar probes;
B. Any suitable fusion imaging software;
C. Various robotic, automatic or semiautomatic arms, such as steppers, that allow to hold ultrasound probes in place and either control or assist in control of their motion;
D. Different energy solutions, which have gained approval by the Food and Drug Administration (FDA) to destroy tissue, for example: Cryoablation Systems, Radiofrequency Systems, probes that employ high frequency ultrasound for tissue destruction, probes that create an electrical field, in which electricity will flow allowing for irreversible electroporation and destruction of tissue, laser probes used for tissue ablation, water vapor "steam" which destroys tissue, photodynamic probes that when activated destroy tissue that contains a pharmaceutical agent, and probes that can deliver nanoparticles, which destroy tissue where it gets infiltrated.

To date no single manufacturer provides an entire solution, but rather the combination of products from several companies are used in order to achieve the desired prostate cancer tumor tissue destruction. In contrast, the approach according to the disclosure includes:

Diagnosis of Prostate Cancer where the tumors, the prostate and close organs such as the seminal vesicles and urethra are identified and contoured on a MRI study—such contouring can be performed by a human being trained to do it or by artificial intelligence, machine learned.

A transperineal approach.

A novel local anesthesia block developed by the inventor.

A ultrasound machine with a dual probe, such as one manufactured by Hitachi-Aloka or BK Ultrasound.

A Stepper, or semi robotic arm with an output that provides positional coordinates, such as the one manufactured by CIVCO.

Fusion software that allows for the co-registration of images between the MRI study findings and the Ultrasound, such as the one created by MIM Software. The software creates a treatment plan. During the treatment, the co-registration is used for real-time monitoring. Optionally, the software can control the ablative or treatment device using safety metrics and records planned vs. executed metrics.

A Cryoablation machine to deliver the freezing and thawing energy, such as the one manufactured by either Endocare-Healthtronics or Galil Medical-BTG. As noted above, other treatment modalities are envisioned by the instant disclosure.

The following describes an embodiment of the system and method according to the disclosure related to an Office-based MRI/US targeted Prostate Cancer Cryoablation. As noted above, in other embodiments cryoablation is noted used for treatment and a different ablative source of energy is used.

Days Before the Procedure

Figure 1:
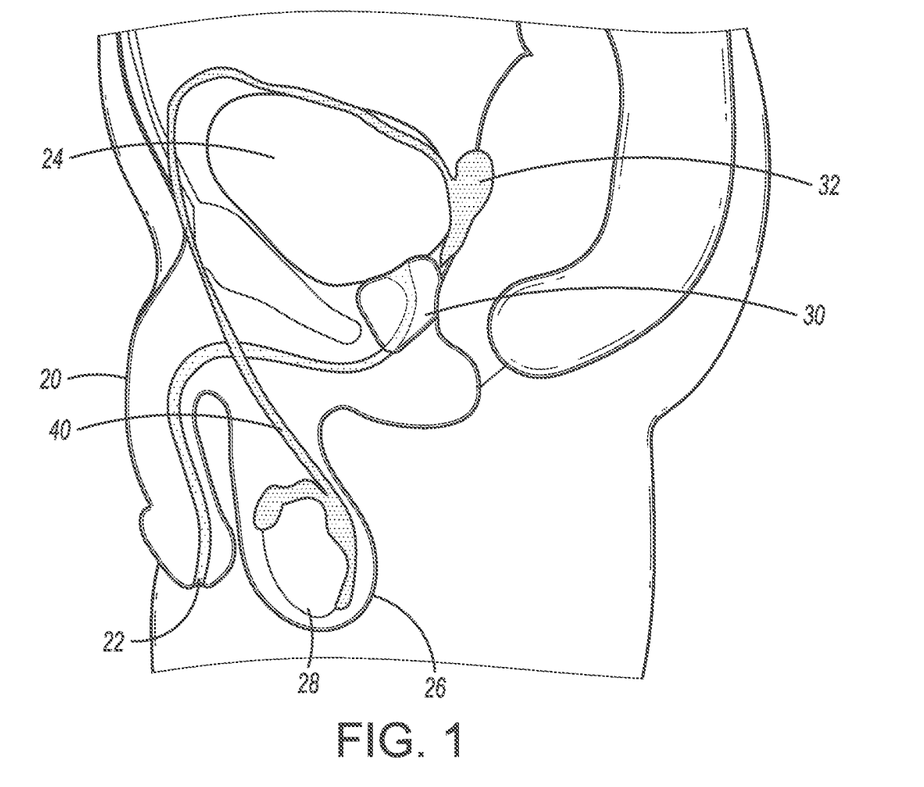
FIG. 1 is a cartoon representation of an image obtained by a multi-parametric MRI.
Figure 2:
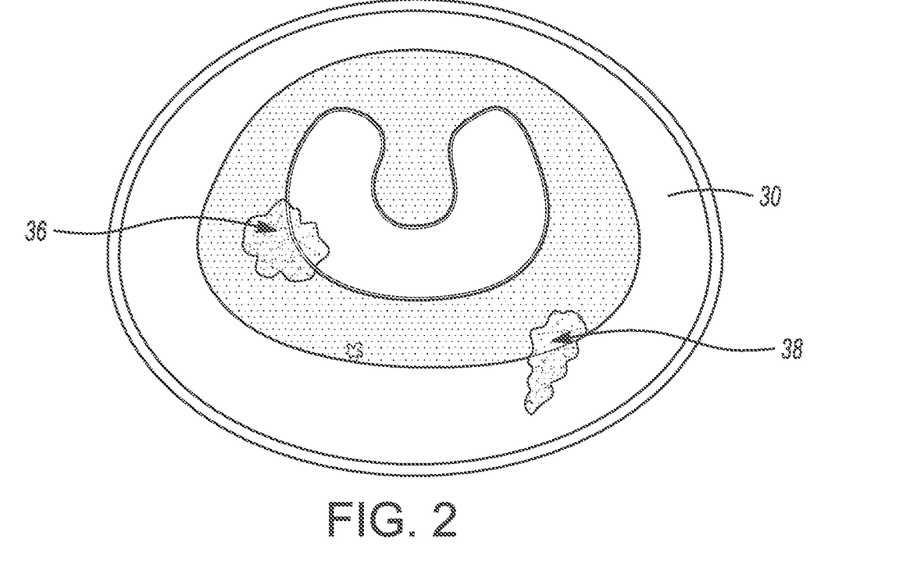
FIG. 2 is a cartoon representation of a different sectional image obtained by the multi-parametric MRI.
Figure 3:
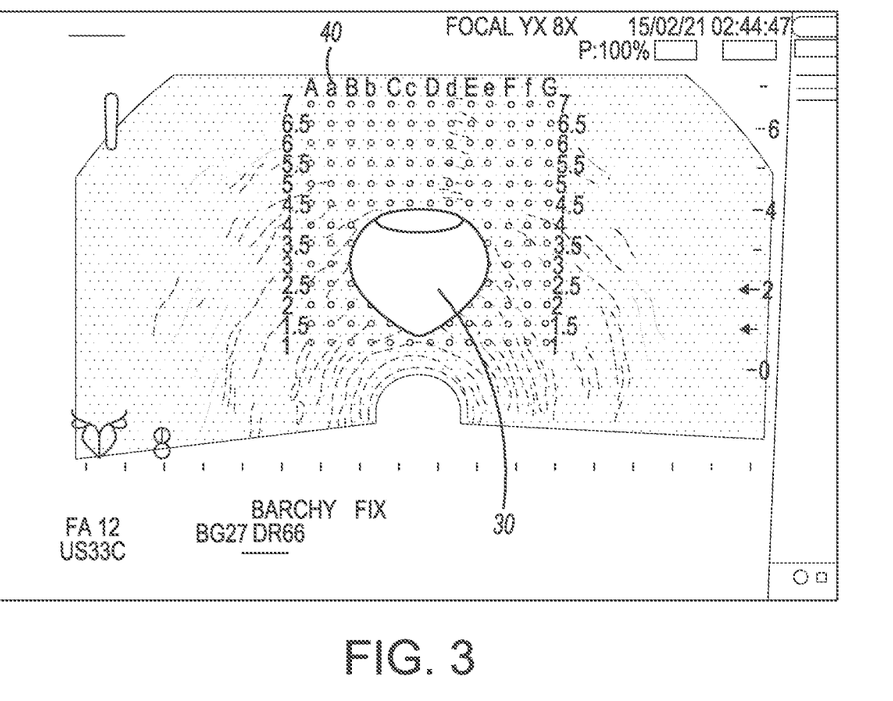
FIG. 3 shows an ultrasound image for use in taking one or more biopsies of prostate tissue.
Figure 4:
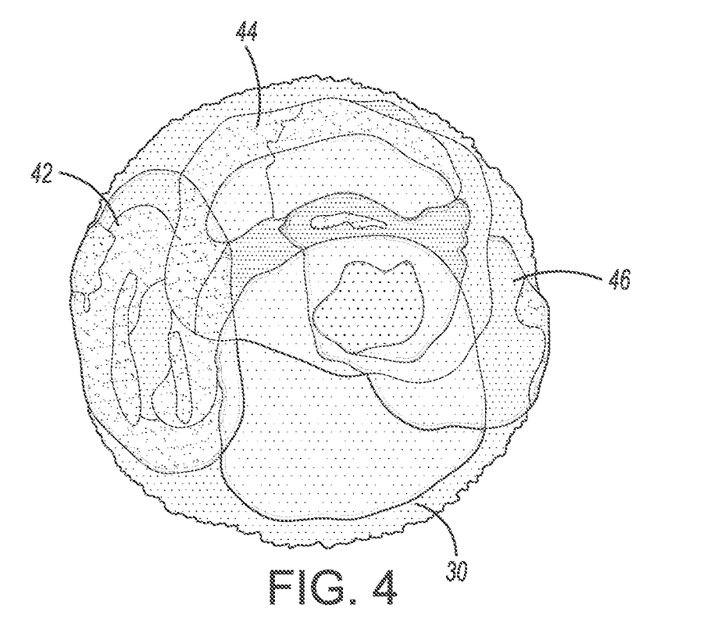
FIG. 4 shows a generated model of the prostate with ice balls (or other ablative energy generation) showing the determined tissue ablation.
Figure 5:
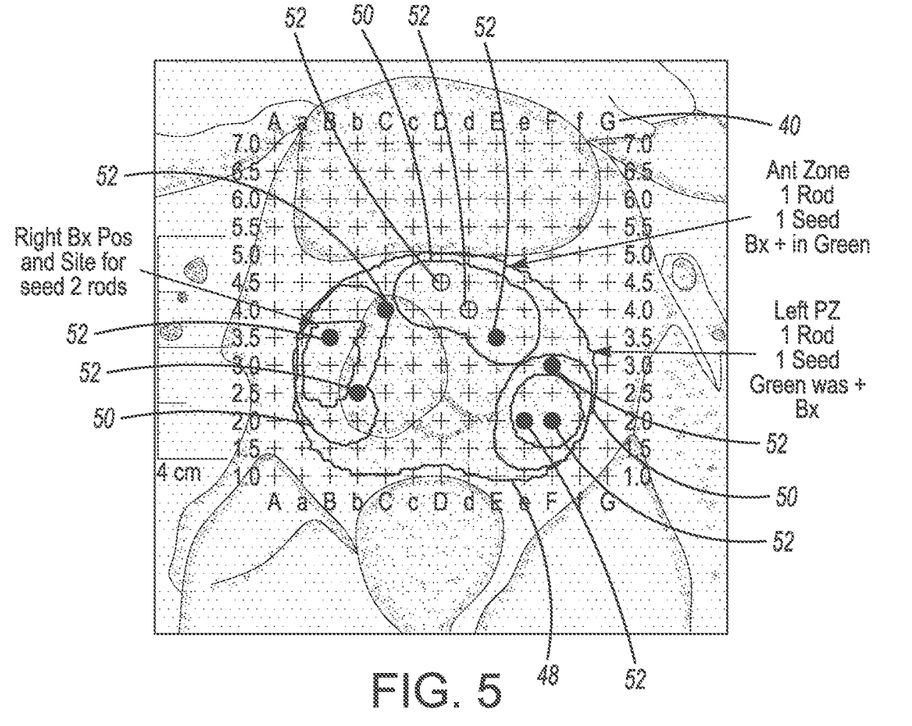
FIG. 5 shows a generated treatment plan superimposed on an MRI image.

1. A multi-parametric MRI has been previously obtained for a biopsy procedure or is requested by the urologist. FIG. 1 is a cartoon representation of an image obtained by the multi-parametric MRI. The penis 20, urethral 22, bladder 24, scrotum 26, testis 28, prostate 30, seminal vesicle 32, vas deferens 34 as well as other anatomical structures are shown. FIG. 2 is a cartoon representation of a different sectional image obtained by the multi-parametric MRI. Regions 36 and 38 of prostate 30 show areas of interest for possible treatment.
2. If desired, using the MRI information and images, guided biopsies of prostate tissue can be taken by a transperineal approach under ultrasound image guidance. FIG. 3 shows an ultrasound image with a cartoon representation of prostate 30 superimposed on the ultrasound image. A grid image 40 corresponding to physical holes in an actual grid is also superimposed on the ultrasound image. The grid image 40 can be used to determine locations of where the biopsies should be taken.
3. The images are uploaded in a computer that is licensed with fusion software to process the MRI and plan treatment. With the uploaded MRI information, thermometrics, statistical modeling and artificial intelligence measures are used for plan generation. FIG. 4 shows a generated model of the prostate 30 with ice balls 42, 44, 46 (or other ablative energy generation) showing the determined tissue ablation.
4. The treatment plan is generated—Prostate gland contouring, prostate cancer lesions and treatment areas are contoured as well. The type, length and precise locations for the cryoprobes are set. The urethra and seminal vesicles are also contoured and put in context with the prostate plan. The planning allows for volumetric estimations. A computerized planning module generates a treatment plan, determining areas of ablation with safety boundaries after calculating the energy, location, number of cryoprobes, and timeframe needed to treat the fibroid volume. FIG. 5 shows a generated treatment plan superimposed on an MRI image. The contour 48 of the prostate and contours 50 of lesions are shown as well as the determined position and placement of ablative energy seeds/rods 52 on grid image 40.

The Day of the Procedure

Figure 6:
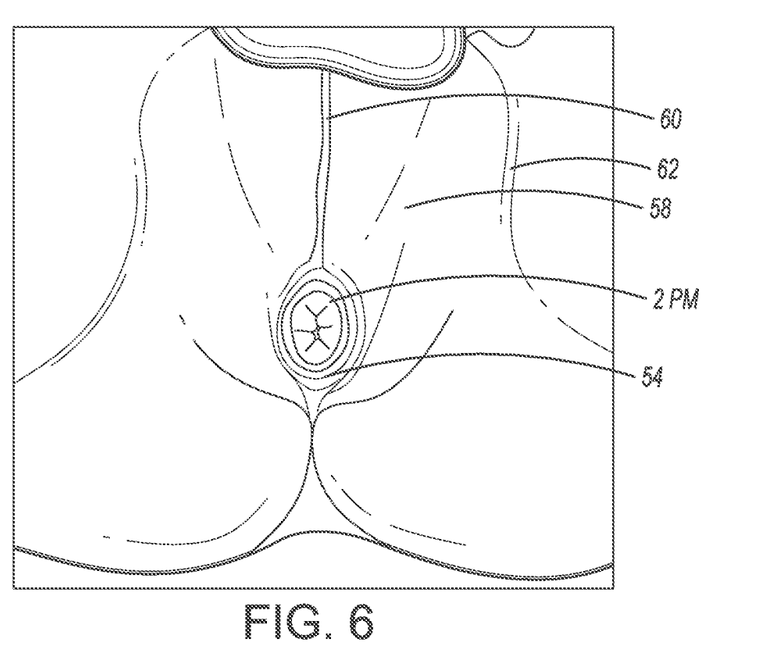
FIG. 6 shows the external anatomical landmarks used for a superficial skin and subcutaneous block.
Figure 7:
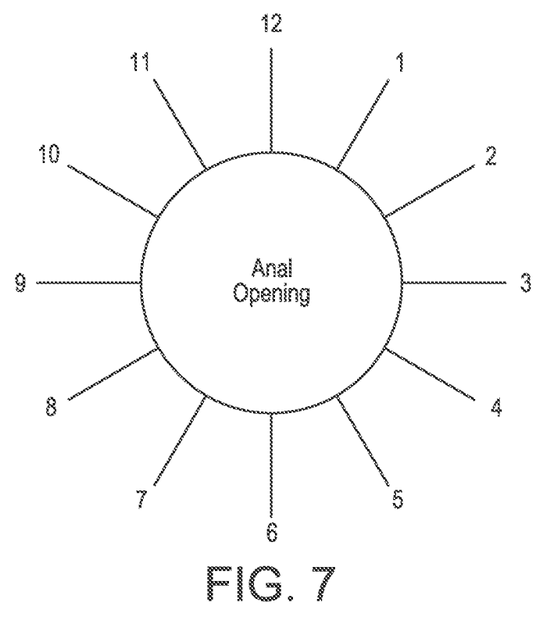
FIG. 7 shows the orientation used for the superficial skin and subcutaneous block.
Figure 8:
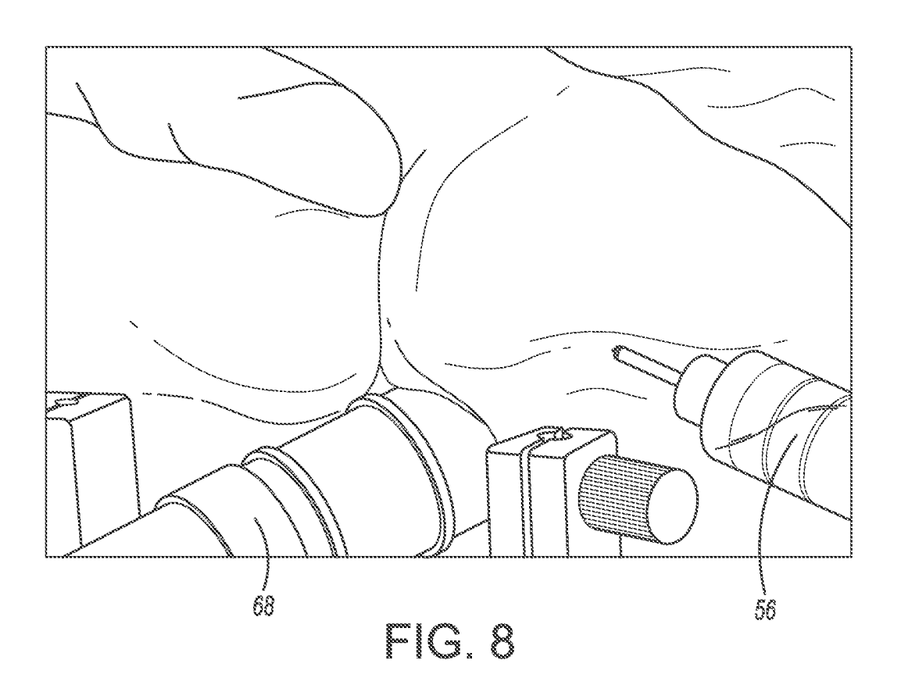
FIG. 8 shows the administering of the superficial skin and subcutaneous block.

1. Patient is instructed to administer a rectal enema, either the morning of or evening before the procedure.
2. Patient is instructed to take daily a prescribed prophylactic antibiotic starting prior to the procedure (e.g. the day before of the procedure) and for a given amount of time (e.g. for 5 days).
3. After obtaining informed consent and about 15 minutes before the procedure, the patient is given the option to take 5 mg or 10 mg of diazepam—a short action antianxiolytic, relaxing agent or another suitable agent.
4. Patient is taken to procedure suite, and placed in a lithotomy position with his legs supported by Allen stirrups. A timed out procedure takes place verifying the place, site and intended treatment and all the team must agree.
5. A superficial skin and subcutaneous block is performed in the perineal areas using lidocaine at 2% or any other suitable agent. With reference to FIGS. 6-8, in an embodiment the infiltration is performed close to the anal verge 54 with a needle 56 (e.g. 20-gauge) starting at the 2 pm location for the right side. About 10 cc of lidocaine are infiltrated from the anal verge 54 covering the perineal space 58, in a rectangular fashion, delimited by the perineal raphe 60 medially, superiorly by the edge of the scrotum 26, laterally by the gluteal crease 60 and inferiorly by the anal verge 54. The procedure is mirrored with same anatomical landmarks on the left side starting at the 10 o'clock position of the anal verge 54. The goal is to cover the area of the perineum where a grid 64 (FIG. 9) will be placed that will guide and hold the cryotherapy probes.

Figure 9:
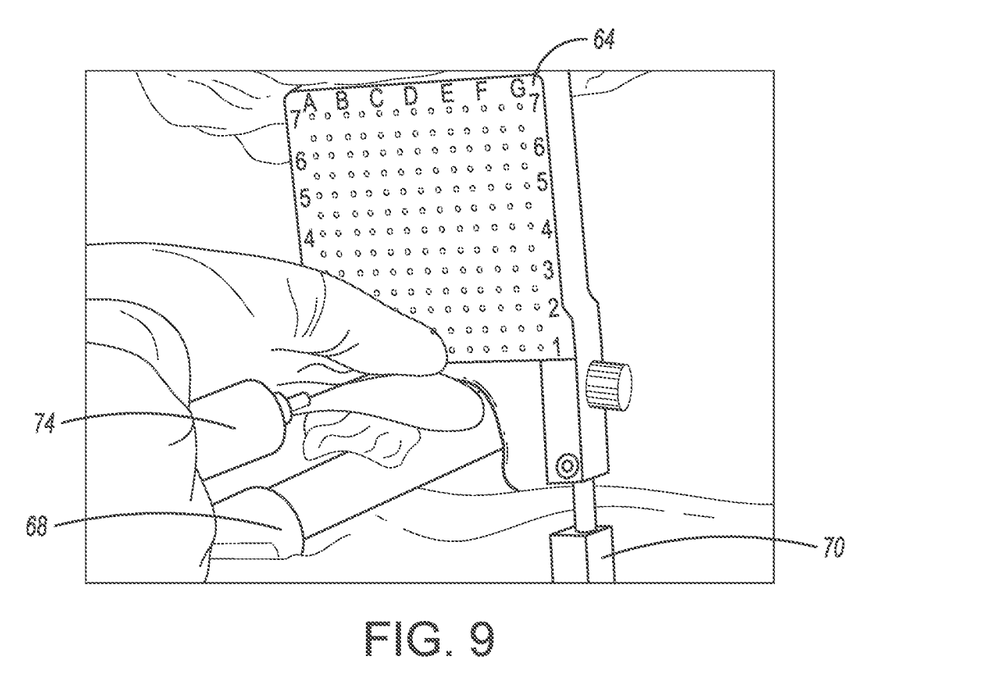
FIG. 9 shows the administering of a deep nerve block.
Figure 10:
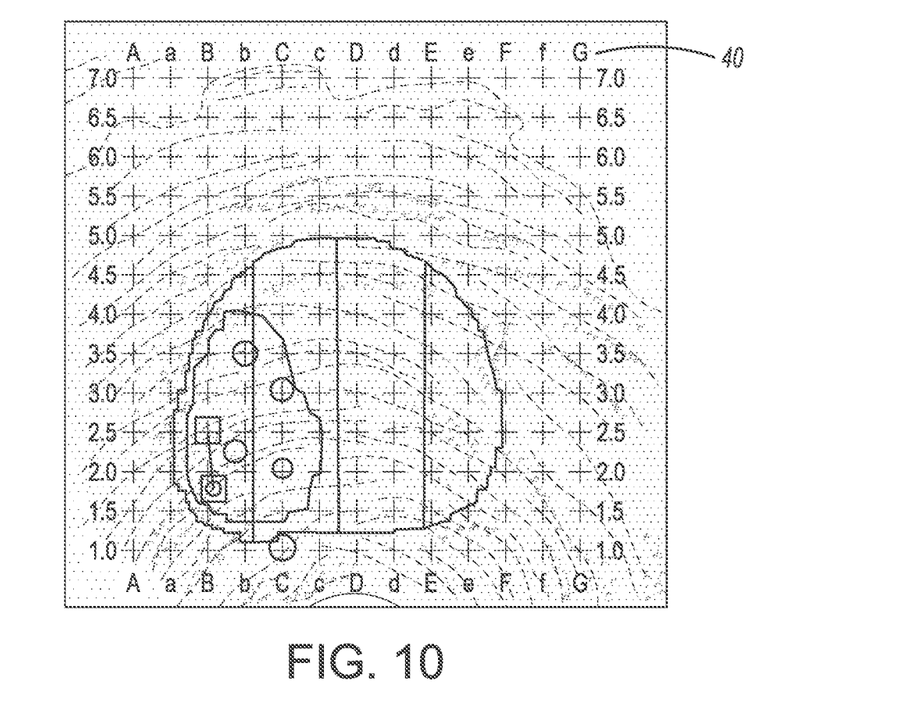
FIG. 10 shows the co-registration of the images from the MRI plan and real-time ultrasound image with the treatment or ablation plan.
Figure 11:
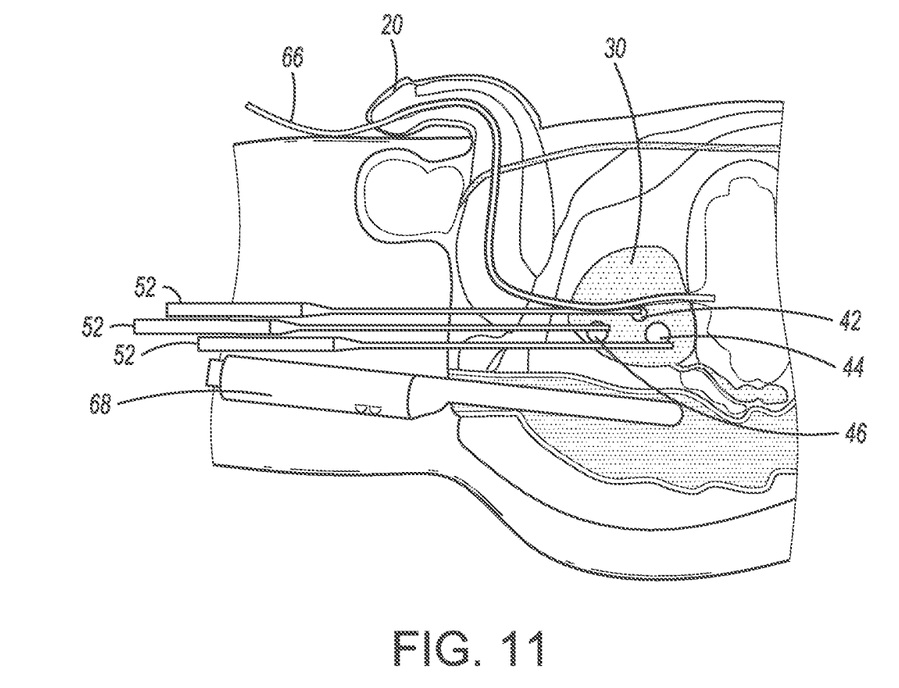
FIG. 11 is a cartoon representation of execution of the treatment plan.
Figure 12:
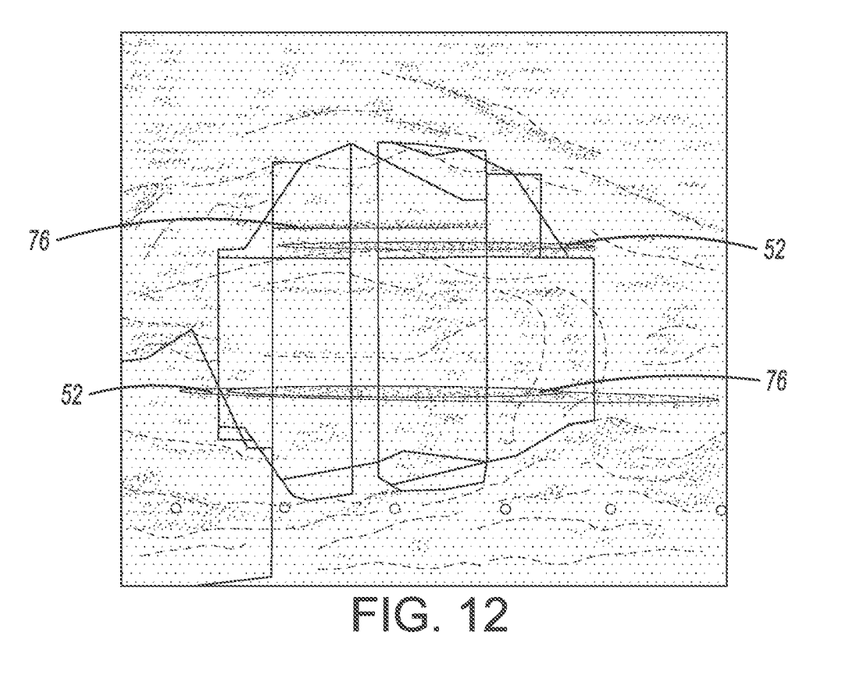
FIG. 12 shows advancement and position of probes used to deliver ablative energy.
Figure 13:
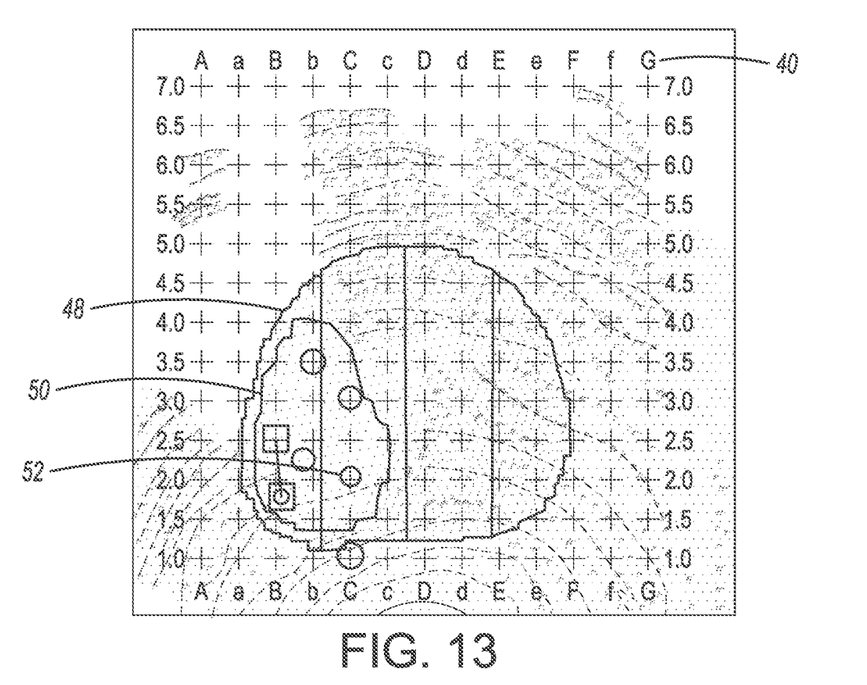
FIG. 13 shows real-time monitoring of the execution of the treatment plan.
Figure 14:
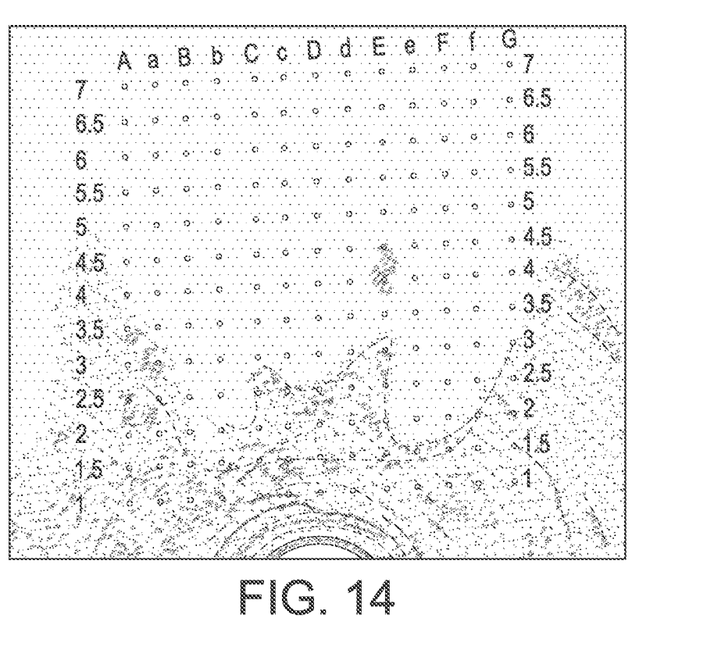
FIG. 14 shows distortion of the ultrasound image resulting from the ablation process.
Figure 15:
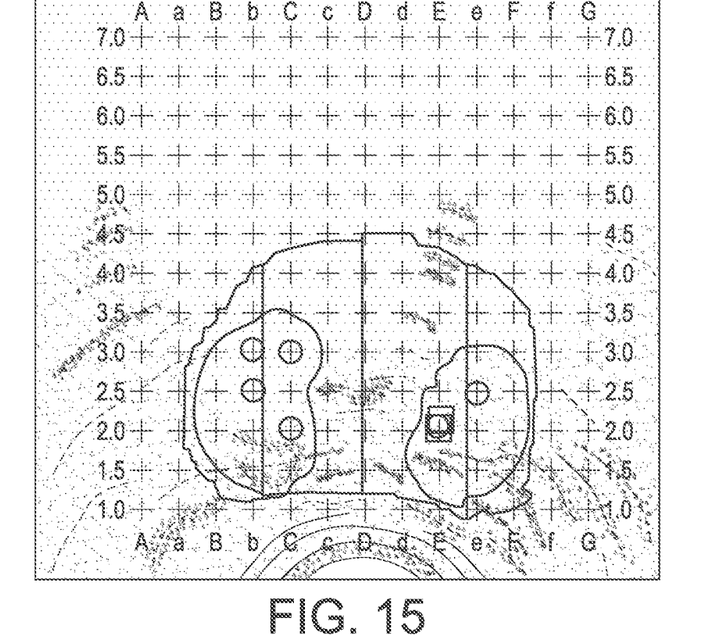
FIG. 15 shows how the disclosed system and method addresses the image distortion of FIG. 14.
Figure 19:
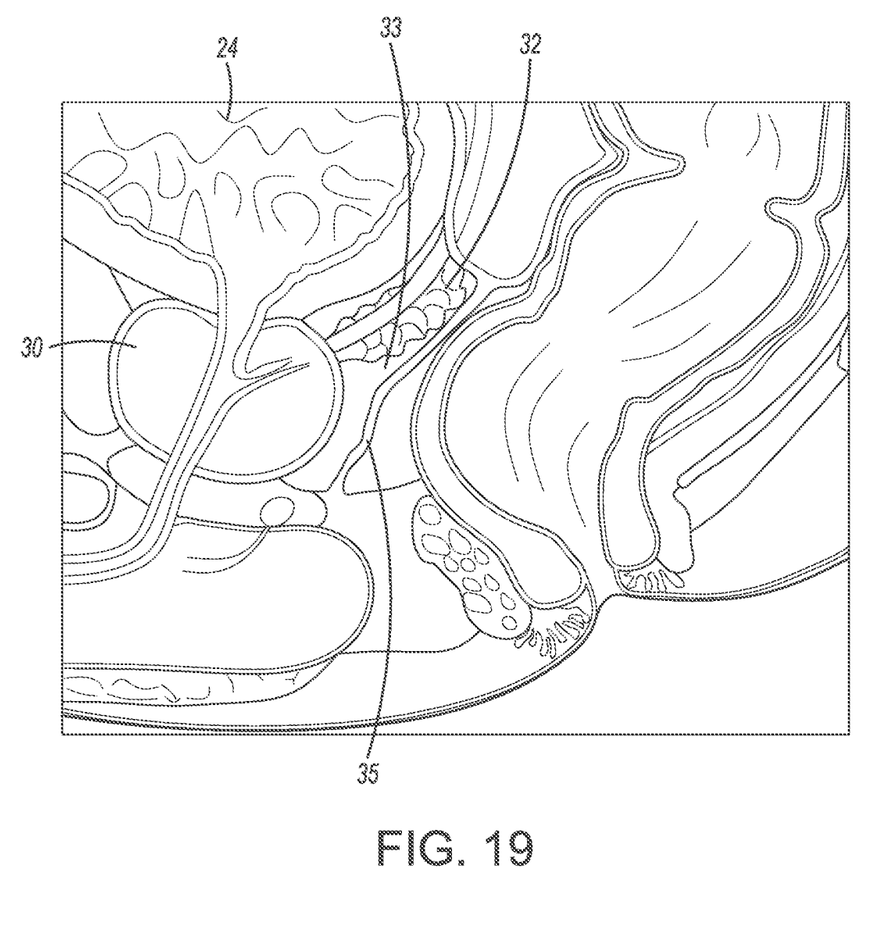
FIG. 19 shows the location of a deep nerve block and various anatomical structures.

6. A few minutes later, a Foley catheter 66 (FIG. 11) is advanced, followed by the ultrasound probe 68. As shown in FIG. 9, probe 68 is secured to a stepper 70 and the prostate is visualized on transverse and sagittal views. As also shown in FIG. 9, a grid 64 (with markings corresponding to the array of holes) is also secured to stepper 70. The markings on grid 64 (and hence the locations of the array of holes) also correspond to grid image 40.
7. A deep nerve block 74 is conducted in sagittal view under ultrasound guidance, infiltrating the cavernosal nerve bundle tissue as well as the periprostatic space (collectively identified as element 33 in FIG. 19). This can be accomplished, for example, with lidocaine 2% using 10 cc for each side. If desired, the grid can be used with the real time ultrasound images to ensure the injection of the agent posterolateral to the prostate capsule and above Denon Villiers fascia 35 bilaterally.
8. If desired, the software runs testing on cryoprobes 52 to ensure proper functioning and records the results.
9. The intraoperative session in the computer using the fusion software is opened, the ultrasound is calibrated and the plan uploaded. This process can be performed manually, semiautomatic or robotically driven by the plan.
10. The co-registration between images from the MRI plan and the real-time ultrasound feed is performed and verified in several axial, transverse and coronal views in real time. FIG. 10 shows the co-registration of the images from the MRI plan and real-time ultrasound image with the treatment or ablation plan.
11. Cryoablation probes 52 are advanced into the perineum and placed in the planned location. If desired, thermocouple sensors or other safety device(s) may be advanced as well. The placement of the probes and/or safety device (s) can be done robotically and automatically by an assistant robotic device. FIG. 11 is a cartoon representation showing placement. As shown in FIG. 12, the actual placement of the seeds/rods 52 (shown in real-time on the ultrasound image) can be compared to the desired position 76 determined by the treatment plan superimposed on the ultrasound image.
12. The prostate, bladder, seminal vesicles and urethra are viewed in real time using the ultrasound images to ensure proper placement and avoidance of other organs.
13. If deemed required by the surgeon, a urethral warmer may also be used.
14. Once the urologic surgeon confirms safety placement of all elements, the treatment is initiated. It begins with a freezing cycle that typically ranges from about 4 to 8 minutes, followed by a warming cycle of about 6 to 10 minutes. The cycles are repeated as needed and determined by the treatment plan. Different times can be used.
15. During the freezing and thawing cycles, the surgeon monitors the destruction by ice balls using the fusion MRI ultrasound imaging (FIG. 13). The practitioner is reassured as the monitoring occurs over the MRI outline and there is constant knowledge of targeted area treatment. Proper perspective of the goals and progress of treatment (as seen in FIG. 15) occurs despite distortion in ultrasound imaging induced by the ablative energy (as seen in FIG. 14).
16. The software captures the treatment session and registers the planned versus accomplished objectives. If there is any safety concern, an alert (e.g. audible and/or visual) can be delivered to the practitioner, who can then adjust the plan, if needed. If the alert goes unattended for a set time frame, the system can enter a pause mode until it receives proper feedback from the practitioner.
17. The software captures critical achieved goals of the treatment session.
18. Upon treatment completion, the software generates a plan for medical record tracking and also generates an encrypted file that can be incorporated into its artificial intelligence modeling framework.
19. Depending on the preferences set up by the patient n their accessory health app, the critical aspect of the treatment plan and its execution will be loaded and available in the app. An example of such an app is the commercially available FOCALYX app.
20. After completion of treatment, the cryoprobes, sensors, grid, stepper and ultrasound probes are removed from the patient and pressure is applied on the perineum. Gauze can be placed to further stop any bleeding and reduce the risk for infection.
21. If used the urethral warmer stays in place for the desired time (e.g. 20 minutes) and then exchanged with a Foley catheter.
22. Patient moves to recovery room and is observed for 20 to 30 minutes or until determined sufficient recovery.
23. Patient is the wheeled to transportation car and medical prescriptions as well as postoperative instructions are provided Post Procedure Follow Up
1. According to preferences set up by the patient in his health accessory record app, the patient can respond to automatic questions that pertain to an uneventful recovery.
2. Both physician and patient could initiate communication at will with each other thru the app should they desire.
3. The app will positively reinforce the patient as he indicates achievement of milestones pertinent to his recovery devised by our clinical pathways and statistical modeling.

Based on the system and method disclosed herein, the benefits can be summarized as follows:
A. Safe and effective implementation of a ablative tissue solution for prostate cancer in the office setting under local anesthesia;
B. Central computer modeling and image processing provides for
 a. Decrease in treatment administration variability
 b. Consistent reproducibility
 c. Decreased adverse events
 d. Reliable clinical care;
C. Precise distinction between ablated and non-ablated tissue based on MRI software generated planning;
D. Upon selection of ablative treatment type, a tailored plan specific to the patient cancer characteristics and the energy source intended to be used is presented;
E. Estimated of plan accomplishment success according to ablated energy that could be applied;
F. Flexibility for the practitioner to choose the desired ablative energy source;
G. Treatment is applied in office setting using fusion imaging solutions and monitored in real-time that overcomes ultrasound image distortion derived from energy source; and
H. Incorporated clinical pathway into the patient recovery process that provides reassurance of progress and to early recognition of any possible adverse event.

Although the disclosure contemplates use of commercially available software with the disclosed system and method, specifically developed algorithms (either in conjunction with the commercially available software or as a substitute) can be used as part of the disclosed system and method. With respect to biopsies, the algorithm estimates cancer risk at a specific prostate location. The model goal is to increase the specificity of the biopsy, enabling the practitioner to harvest tissue samples where it is more likely than not of harboring prostate cancer.

The model should incorporate standard variables such as age (age), PSA levels (PSA), family history of prostate cancer (FHx), digital rectal exam information (dre), overall piRads score of the MRI (piR), history of diagnosis of prostate cancer for the active surveillance patient (preDxPCA), history of prior treatment and area treated (pretxloc) plus specific findings in areas closest to the regions of interest in regards of dynamic contrast enhancement at initial enhancement (icon) and 1 cm away (10 mmicon).

In an exemplary embodiment, the model incorporates specific changes in T2W imaging (t2w), apparent diffusion coefficient (ADC) and restriction signal (res) and the next sequence changes in dynamic contrast enhancement of the areas of interest (nscon) and of the prostate transitional zone (TZnscon).

Figure 16:
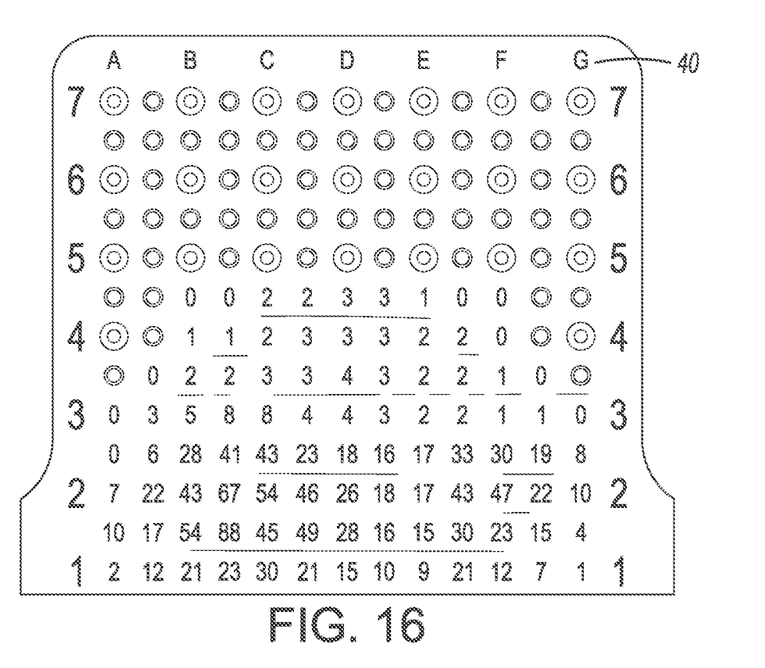
FIG. 16 shows calculated estimated probability of cancerous tissue at a given prostate location.

The predictions are given per specific location and estimates are provided directly into the fusion software so that when the MRI image and real time ultrasound imaging are fused, grid image 40 shows the percentage risk of having prostate cancer at a given grid location. This is shown in FIG. 16 and can be used by the practitioner to determine where to take biopsies.

With respect to developing the treatment plan, one exemplary model evaluates the information from the biopsy results and the MRI findings along with traditional variables (as set forth above). The model provides the best location to place the probes given the dimension of the lesions and area of intended treatment area. This model incorporates the biopsy results but also the probabilities of cancer in the adjacencies of the detected tumor.

In another exemplary model for developing a treatment plan, the model provides for the safety of the procedure calculating and showing the expected temperatures around the killing tissue zones (TxPTemps) and their boundaries and includes several measures such as areas and sizes of both lesion (dxlessize, dxlesvol) and treatment area (txvol, txsize), respectively. This model controls for the distance from the edges of the treatment area to the neurovascular bundles and rectum (degnvb, degree) and the distance from the tip of the probes to the bladder neck and from the end of the iceball to the urethra (cordPbUta, cordPbBN). To date, the outcomes of the model have been correlated to measured temperatures in 300 patients thus a thermometric prediction is obtained at each point of the grid. Control temperatures can be used to verify the precision of the model and all this information is incorporated into machine learning algorithms.

Figure 17:
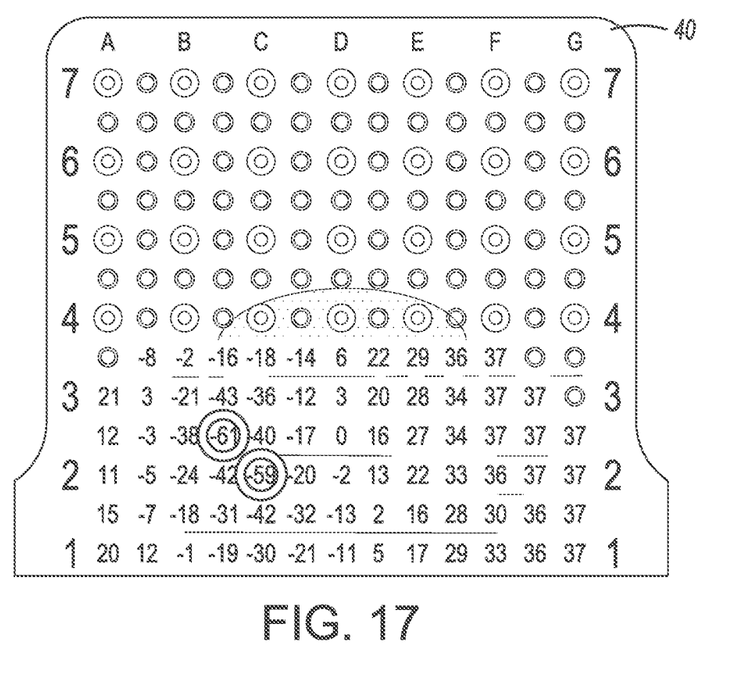
FIG. 17 shows calculated estimated tissue temperature if probes are placed as determined by the disclosed system and method.
Figure 18:
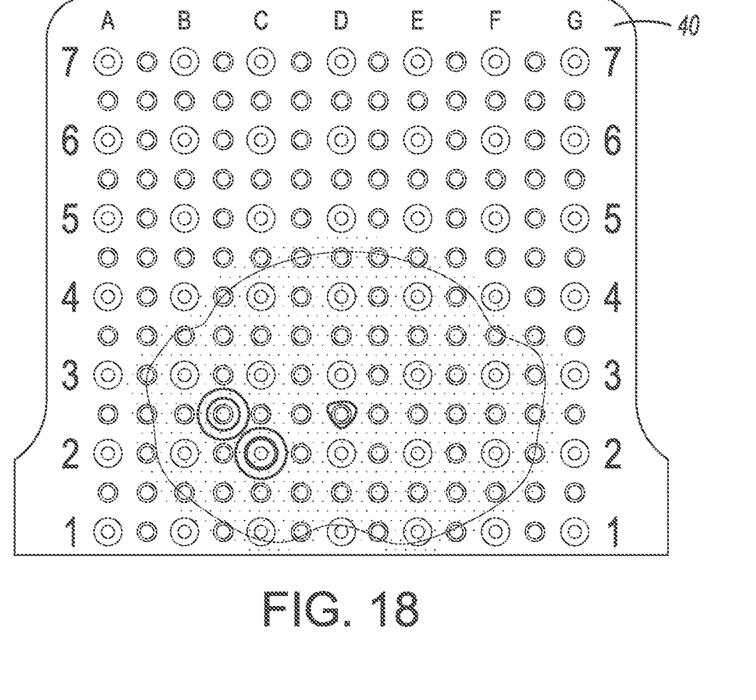
FIG. 18 shows the calculated placement position and number of probes as determined by the disclosed system and method.

FIG. 17 shows the calculated estimated temperatures at each grid image 40 location if probes are placed as suggested by the model. FIG. 18 shows the calculated optimal probe number and placement.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains. Accordingly, all expedient modifications readily attainable by one versed in the art from the disclosure set forth herein that are within the scope and spirit of the present disclosure are to be included as further embodiments of the present disclosure.

What is claimed is:

1. A method for prostate cancer treatment under local anesthesia, the method comprising:
    creating a superficial skin and subcutaneous block in a perineal area of a patient by administering a first anesthetizing agent;
    creating a deep nerve block under ultrasound guidance by administering a second anesthetizing agent, the second anesthetizing agent infiltrating cavernosal nerve bundle tissue and periprostatic space;
    obtaining multi-parametric MM imaging of the prostate and surrounding tissue;
    creating a treatment plan based on the MM imaging;
    obtaining ultrasound imaging of the prostate and surrounding tissue with an ultrasound probe;
    producing fusion imaging by co-registration of the MRI imaging and ultrasound imaging, the fusion imaging including contours of the prostate and contours of prostate cancer lesions, wherein the fusion imaging shows the treatment plan with a planned location of a treatment probe for ablating prostate tissue;
    inserting the treatment probe to the planned location;
    utilizing the treatment plan to ablate prostate tissue,
    wherein the treatment plan is created based on a model calculating and showing expected temperatures around tissue ablation zones.

2. The method of claim 1, wherein the first and second anesthetizing agent are lidocaine solutions.

3. The method of claim 1, wherein the patient is placed in a lithotomy position.

4. The method of claim 1, wherein the superficial skin and subcutaneous block is created by administering the first anesthetizing agent in a first perineal space, the first perineal space delimited by a perineal raphe medially, superiorly by an edge of a scrotum, laterally by a first gluteal crease and inferiorly by an anal verge; and administering the first anesthetizing agent in a second perineal space, the second perineal space delimited by the perineal raphe medially, superiorly by the edge of the scrotum, laterally by a second gluteal crease opposite the first gluteal crease, and inferiorly by the anal verge.

5. The method of claim 1, further comprising real-time monitoring of the ablation with the ultrasound imaging.

6. The method of claim 5, wherein the ultrasound imaging is obtained with a transrectal ultrasound probe.

7. The method of claim 6, wherein the ultrasound probe is attached to a stepper to control position and movement of the ultrasound probe.

8. The method of claim 7, wherein a grid is attached to the stepper, the grid provided with indicia for identifying holes in the grid.

9. The method of claim 8, wherein the fusion imaging includes an image of the grid.

10. The method of claim 9, wherein the treatment probe uses: high frequency ultrasound for tissue destruction; an electrical field, in which electricity flows allowing for irreversible electroporation and destruction of tissue; laser energy for tissue ablation; water vapor "steam" for tissue destruction; photodynamic energy that when activated destroy tissue that contains a pharmaceutical agent; nanoparticles, which destroy tissue; or cryoablation for tissue destruction.

11. The method of claim 9, further comprising comparing the actual position of the treatment probe to the planned location.

12. The method of claim 11, further comprising monitoring ablation of tissue by comparing the treatment plan shown on the fusion imaging to tissue destruction shown on the fusion imaging.

13. A method for prostate cancer treatment under local anesthesia, the method comprising:
- creating a superficial skin and subcutaneous block in a perineal area of a patient by administering a first anesthetizing agent;
- creating a deep nerve block under ultrasound guidance by administering a second anesthetizing agent, the second anesthetizing agent infiltrating cavernosal nerve bundle tissue and periprostatic space;
- obtaining multi-parametric MM imaging of the prostate and surrounding tissue;
- obtaining ultrasound imaging of the prostate and surrounding tissue with a transrectal ultrasound probe attached to a stepper to control position and movement of the ultrasound probe, wherein a grid is attached to the stepper and the grid is provided with indicia for identifying holes in the grid;
- producing fusion imaging by co-registration of the MRI imaging and ultrasound imaging, the fusion imaging including an image of the grid and contours of the prostate and contours of prostate cancer lesions, wherein the fusion imaging shows a treatment plan with a planned location of a treatment probe for ablating prostate tissue;
- inserting the treatment probe to the planned location;
- comparing the actual position of the treatment probe to the planned location;
- ablating prostate tissue; and
- monitoring ablation of tissue by comparing the treatment plan shown on the fusion imaging to tissue destruction shown on the fusion imaging,
- wherein the treatment plan is created based on a model calculating and showing expected temperatures around tissue ablation zones.

14. The method of claim 13, wherein the model is based on lesion location and lesion volume and treatment location and treatment volume.

15. The method of claim 14, wherein the model is based on distances from edges of a treatment zone defined by the treatment location and treatment volume to anatomical structures.

* * * * *